United States Patent [19]

Kelly

[11] Patent Number: 5,204,018
[45] Date of Patent: Apr. 20, 1993

[54] LIQUID CRYSTALS

[75] Inventor: Stephen Kelly, Möhlin, Switzerland

[73] Assignee: Hoffmann-La Roche Inc., Nutley, N.J.

[21] Appl. No.: 643,965

[22] Filed: Jan. 22, 1991

[30] Foreign Application Priority Data

Feb. 1, 1990 [CH] Switzerland .................. 326/90

[51] Int. Cl.$^5$ .................. C09K 19/30; C09K 19/34; C09K 19/54; C07D 239/02
[52] U.S. Cl. .................. 252/299.63; 252/299.61; 252/299.66; 252/299.67; 252/299.62; 252/299.5; 560/64; 560/65; 560/102; 544/224; 544/239; 544/298; 546/339; 546/342; 546/340; 568/647; 568/631; 568/642; 549/369; 549/370
[58] Field of Search .................. 252/299.63, 299.67, 252/299.5, 299.62, 299.61, 299.66; 560/64, 65; 558/416, 425; 544/298; 546/339, 340; 568/647, 631, 642; 549/369, 370

[56] References Cited

U.S. PATENT DOCUMENTS

| 4,035,056 | 7/1977 | Coates et al. .............. 252/299.66 X |
| 4,627,933 | 12/1986 | Eidenschink et al. .......... 252/299.6 |

FOREIGN PATENT DOCUMENTS

| 0387032 | 9/1990 | European Pat. Off. . |
| 3509170 | 9/1986 | Fed. Rep. of Germany . |
| 2612182 | 8/1988 | France . |
| 0118789 | 6/1985 | Japan . |
| 8802357 | 4/1988 | PCT Int'l Appl. . |
| 91/03450 | 3/1991 | PCT Int'l Appl. . |

OTHER PUBLICATIONS

Kelly, S. M., Mol. Cryst. Liq. Cryst. vol. 24, pp. 27-35 (1991) (Presented at The Thirteenth International Liquid Crystal Conference, Vancouver, British Columbia, Canada, 22-27, Jul. 1990).
Derwent Abstract No. 91-074773/11 for WO 91/03450.
Influence of Molec. Structure Gray et al, Editor Liquid Crystals & Plastic Crystals vol. 1, 1974.
Kelly, S. M., "The Synthesis and Liquid Crystal Transition Temperature..." Presentation at British Colombia, Canada (Jul. 1990).
R. Weidauer, R. Frach and H.-J. Deutscher, Doktoranden-kolloquim "Anisotrope Fluide", (Berlin 1990).

Primary Examiner—Robert L. Stoll
Assistant Examiner—C. Harris
Attorney, Agent, or Firm—George M. Gould; William H. Epstein; John J. Schlager

[57] ABSTRACT

Compounds of the formula

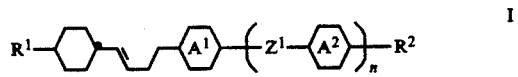

I wherein n stands for the number 0 or 1; $R^1$ denotes a group $R^3$ or $R^3$—$A^3$—$Z^2$— and $R^2$ denotes a group $R^4$ or $R^4$—$A^4$—$Z^3$—; ring $A^1$ signifies unsubstituted or halogen-, cyano- and/or methyl-substituted 1,4-phenylene in which optionally 1 CH group or 2 CH groups is/are replaced by nitrogen; $A^3$, $A^4$ and ring $A^2$ each independently represent unsubstituted or halogen-, cyano- and/or methyl-substituted 1,4-phenylene in which optionally 1 CH group or 2 CH groups is/are replaced by nitrogen or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$, $Z^2$ and $Z^3$ each independently signify a single covalent bond, —COO—, —OOC—, —CH$_2$O—, —OCH$_2$—, —CH$_2$CH$_2$—, —CH≡C—, —(CH$_2$)$_3$O—, —O(CH$_2$)$_3$—, —(CH$_2$)$_4$— or the trans form of —CH=CH—CH$_2$CH$_2$—, —CH$_2$CH$_2$—CH=CH—, —CH=CH—CH$_2$O— or —OCH$_2$—CH=CH—; $R^3$ and $R^4$ each independently denote halogen, cyano, —NCS, —CF$_3$, —OCF$_3$ or alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX—; and X signifies halogen, cyano or methyl, as well as liquid crystalline mixtures which contain such compounds and their use for electro-optical purposes.

10 Claims, No Drawings

LIQUID CRYSTALS

The present invention is concerned with novel (4E-cyclohexyl-3-butenyl)aryl derivatives, liquid crystalline mixtures which contain such compounds as well as their use for electro-optical purposes.

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells ("twisted nematic") and STN cells ("super-twisted nematic") having a twisted nematic structure, SBE cells ("super birefringence effect"), phase change cells having a cholesteric-nematic phase transition and OMI cells ("optical mode interference"). The most common indicating devices are based on the Schadt-Helfrich effect and have a twisted nematic structure.

Further, electro-optical devices based on chiral tilted smectic liquid crystals have been proposed in Appl. Phys. Lett. 36, 899 (1980) and in Recent Developments in Condensed Matter Physics 4, 309 (1981). In this case the ferroelectric properties of these materials are made use of. As the tilted smectic phases there are suitable, for example, smectic C, F, G, H, I and K phases. There are generally preferred smectic C phases which permit especially high response speeds. The chiral tilted phases are usually denoted by $S_C^*$, $S_F^*$ etc., with the asterisk indicating the chirality.

The liquid crystal materials must have a good chemical and thermal stability and a high stability towards electric fields and electromagnetic radiation. Further, the liquid crystal materials should have low viscosity and in the cells should give short response times, low threshold potentials and a high contrast. Furthermore, at the usual operating temperatures they should have a suitable mesophase, for example a nematic, cholesteric or chiral tilted smectic phase. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. Besides the general interest in liquid crystal materials having a high optical anisotropy, there has recently been an increased interest in materials having a low optical anisotropy, especially for actively addressed liquid crystal indicators, e.g. in the case of TFT applications (thin film transistor) in television sets. On the other hand, chiral tilted smectic liquid crystals should have a sufficiently high spontaneous polarization.

In order to optimize the properties, liquid crystals are generally used as mixtures of several components. It is therefore important that the components have a good miscibility with one another. Cholesteric mixtures can preferably consist of one or more optically active dopants and a nematic liquid crystal material and ferroelectric liquid crystals can preferably consist of one or more optically active dopants and a liquid crystal material having a tilted smectic phase.

The present invention provides compounds of the general formula

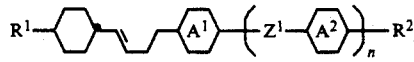

wherein n stands for the number 0 or 1; $R^1$ denotes a group $R^3$ or $R^3—A^3—Z^2—$ and $R^2$ denotes a group $R^4$ or $R^4—A^4—Z^3—$; ring $A^1$ signifies unsubstituted or halogen-, cyano- and/or methyl-substituted 1,4-phenylene in which optionally 1 CH group or 2 CH groups is/are replaced by nitrogen; $A^3$, $A^4$ and ring $A^2$ each independently represent unsubstituted or halogen-, cyano- and/or methyl-substituted 1,4-phenylene in which optionally 1 CH group or 2 CH groups is/are replaced by nitrogen or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$, $Z^2$ and $Z^3$ each independently signify a single covalent bond, —COO—, —OOC—, —CH$_2$O—, —OCH$_2$—, —CH$_2$CH$_2$—, —C≡C—, —(CH$_2$)$_3$O—, —O(CH$_2$)$_3$—, —(CH$_2$)$_4$— or the trans form of —CH=CH—CH$_2$CH$_2$—, —CH$_2$CH$_2$—CH=CH—, —CH=CH—CH$_2$O— or —OCH$_2$—CH=CH—; $R^3$ and $R^4$ each independently denote halogen, cyano, —NCS, —CF$_3$, —OCF$_3$ or alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX—; and X signifies halogen, cyano or methyl.

It has surprisingly been found that the compounds of formula I, which have a butene bridging group between a cyclohexane ring and an aromatic ring $A^1$, have a pronounced tendency to form liquid crystalline phases in spite of the high flexibility of the bridging group. The optically inactive compounds of formula I have for the most part a nematic, a smectic A and/or a tilted smectic (primarily $S_C$) Phase and the optically active compounds of formula I have for the most part a cholesteric, a smectic A and/or a chiral tilted smectic (primarily $S_C^*$) phase. These mesophase types are especially suitable for increasing nematic, cholesteric or chiral tilted smectic phases in liquid crystal mixtures. Compounds of formula I which have a highly ordered smectic phase, e.g. a smectic B phase, also have, however, a good miscibility with usual liquid crystal materials. The present invention accordingly provides a wide range of novel components and mixtures for the further optimization and modification of liquid crystal materials.

The compounds of formula I possess a high chemical stability and a high stability towards electric and magnetic fields. They are colourless, can be manufactured readily and have a good solubility with one another and in known liquid crystal materials. Further, they possess low viscosities and give short response times in indicating devices.

The properties of the compounds of formula I can be varied in wide ranges depending on the number and significance of the rings and of the substituents. For example, aromatic rings lead to higher values of the optical anisotropy and saturated rings lead to lower values of the optical anisotropy. An increase in the clearing point can be achieved, for example, by the introduction of one or more additional rings. Polar end groups such as cyano, halogen, —NCS, —CF$_3$ or —OCF$_3$ and rings such as pyrimidine-2,5-diyl, trans-1,3- dioxane-2,5-diyl etc. increase the dielectric anisotropy, rings such as pyridazine-3,6-diyl, 1-cyano-trans-1,4-cyclohexylene, 2,3-dicyano-1,4-phenylene etc. reduce the dielectric anisotropy and lateral halogen and cyano substituents contribute to the dielectric constants not only parallel to but also perpendicular to the longitudinal axis of the molecule, which can be utilized depending on the substitution pattern to increase or reduced the dielectric anisotropy. Further, the mesophase range can be modified, a possible tendency to form highly ordered smectic phases can be largely suppressed and frequently the solubility can also be improved by lateral substituents on one or more rings. Furthermore, the elastic properties, the threshold potentials, the response times, the mesophases etc. can be modified further by a C=C double bond in the side-chain.

The compounds in accordance with the invention therefore permit a further optimization of liquid crystal mixtures and a modification of the electro-optical properties in a wide range according to the desired properties.

The term "halogen" denotes in the scope of the present invention fluorine, chlorine, bromine or iodine, preferably fluorine or chlorine.

The term "unsubstituted or halogen-, cyano- and/or methyl-substituted 1,4-phenylene in which optionally 1 CH group or 2 CH groups is/are replaced by nitrogen" embraces groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano-1,4-phenylene, 2-methyl-1,4-phenylene, pyridine-2,5-diyl, pyrazine-2,5-diyl, pyrimidine-2,5-diyl, pyridazine-3,6-diyl and the like. 1,4-Phenylene, 2-fluoro-1,4-phenylene, 2,3-difluoro-1,4-phenylene, pyridine-2,5-diyl, pyrazine- 2,5-diyl and pyrimidine-2,5-diyl are preferred groups.

The term "tetralin-2,6-diyl" denotes 1,2,3,4-tetrahydronaphthalene-2,6-diyl. The term "trans-decalin-2,6-diyl" embraces 2,6-disubstituted groups derived from trans-decahydronaphthalene, especially (4aαH,8aβH)-decahydronaphthalene-2α,6β-diyl.

The term "alkyl in which optionally one >CH—CH< is replaced by >C=C< and/or one methylene group or two non-adjacent methylene groups is/are replaced by —O—, —COO— and/or —OOC— and/or optionally one methylene group is replaced by —CHX—" embraces straight-chain and branched (optionally chiral) residues such as alkyl, 1E-alkenyl, 3E-alkenyl, 4-alenyl, alkenyl having a terminal double bond, alkoxy, 2E-alkenyloxy, 3-alkenyloxy, alkenyloxy having a terminal double bond, alkoxyalkyl, alkenyloxyalkyl, alkoxycarbonyl, alkoxycarbonylalkoxy, alkanoyloxy, 1-haloalkyl, 2-haloalkyl, 2-haloalkoxy, 2-haloalkoxycarbonyl, 1-cyanoalkyl, 2-cyanoalkyl, 2-cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Examples of preferred straight or branched chain residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, allyloxymethyl, methoxycarbonyl, ethoxycarbonyl, propyloxycarbonyl, 1-methylpropyloxycarbonyl, 1-(methoxycarbonyl)ethoxy, 1-(ethoxycarbonyl)ethoxy, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, 2-chloropropyloxy, 2-fluorobutyloxy, 2-fluoropropyloxycarbonyl, 2-fluorobutyloxycarbonyl, 2-fluoropentyloxycarbonyl, 2-fluoro-3-methylbutyloxycarbonyl, 2-fluoro-4-methylpentyloxycarbonyl, 2-chloropropyloxycarbonyl, 1-cyanopropyl, 1-cyanopentyl, 2-cyanopropyl, 2-cyanopentyl, 2-cyanopropyloxy, 2-cyanobutyloxy, 2-cyanopentyloxy, 2-cyanohexyloxy, 2-cyanopropyloxycarbonyl, 2-cyanobutyloxycarbonyl, 2-cyano-3-methylbutyloxycarbonyl, 2-cyano-4-methylpentyloxycarbonyl and the like.

Preferred compounds of formula I are the compounds of the general formulae

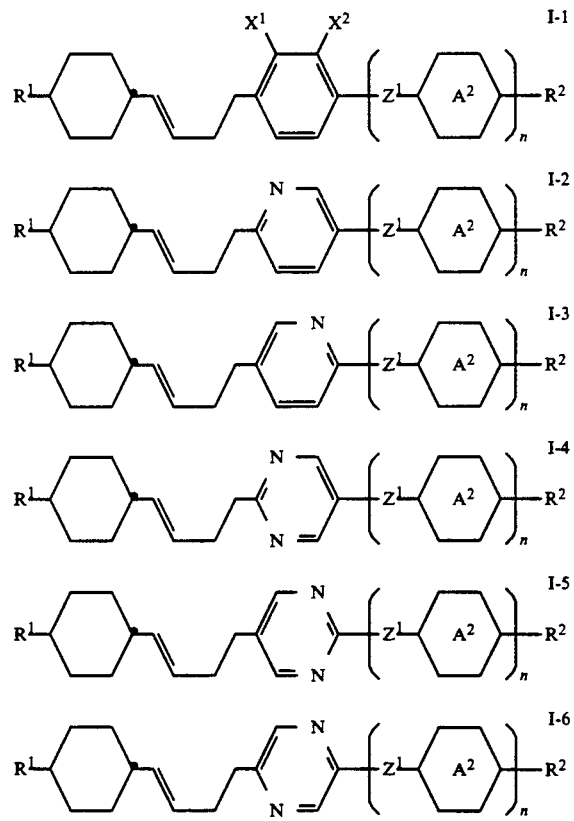

wherein n, $R^1$, $R^2$, $Z^1$ and ring $A^2$ have the above significances and $X^1$ and $X^2$ each independently denote hydrogen, halogen, cyano or methyl.

In formulae I and I-1 to I-6 above, ring $A^2$ preferably stands for unsubstituted 1,4-phenylene or 1,4-phenylene which maybe monosubstituted or 2,3-disubstituted with halogen, cyano and/or lower alkyl, preferably methyl trans- -1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl or trans-decalin-2,6-diyl. In formulae I and I-1, $A^2$ denotes pyridine-2,5-diyl, pyrimidine-2,5-diyl or pyrazine-2,5-diyl.

Preferably, $A^3$ and $A^4$ each independently stand for trans-1,4-cyclohexylene or for unsubstituted or halogen-, cyano- and/or methyl-substituted 1,4-phenylene, most preferably, for trans-1,4-cyclohexylene.

Preferably, $Z^1$, $Z^2$ and $Z^3$ each stand for a single covalent bond or one of the groups $Z^1$, $Z^2$ and $Z^3$ (preferably $Z^1$) also stands for —COO—, —OOC—, —CH$_2$O—, —OCH$_2$—, —CH$_2$CH$_2$—, —C≡C—, —CH$_2$)$_3$O—, —O(CH$_2$)$_3$—, —(CH$_2$)$_4$— or the trans form of —CH=CH—CH$_2$CH$_2$—, —CH$_2$CH$_2$—CH=CH—, —CH=CH—CH$_2$O— or —OCH$_2$—CH=CH—.

The bicyclic and the tricyclic compounds of formulae I and I-1 to I-6 are preferred basic materials for liquid crystalline mixtures. In the bicyclic compounds n stands for the number 0, $R^1$ stands for $R^3$ and $R^2$ stands for $R^4$. In the tricyclic compounds n stands for the number 1, $R^1$ stands for $R^3$ and $R^2$ stands for $R^4$ or n stands for the number 0, $R^1$ stands for $R^3$—$A^3$—$Z^2$— and $R^2$ stands for $R^4$ or n stands for the number 0, $R^1$ stands for $R^3$ and $R^2$ stands for $R^4$—$A^4$—$Z^3$—. Compounds having 4 or 5 rings are, however, preferred when high clearing points are desired (e.g. for use as dopants for increasing the clearing point or as a stationary phase in gas chromatography).

Examples of especially preferred sub-groups of compounds of formula I are the compounds of the general formulae

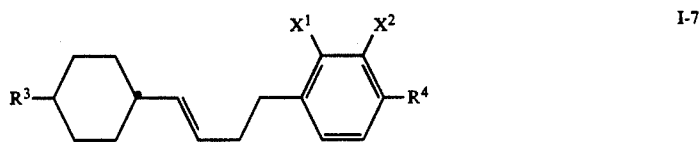

I-7

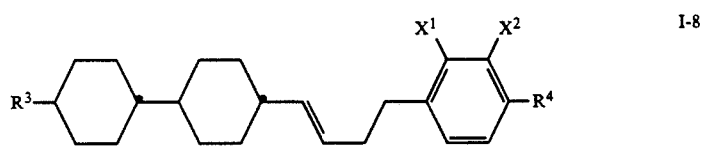

I-8

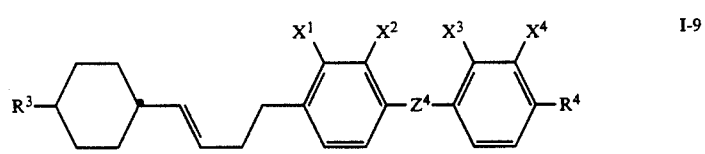

I-9

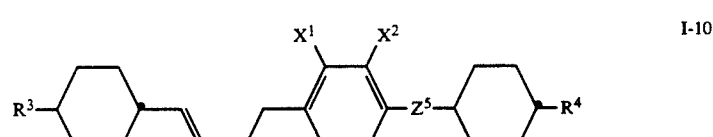

I-10

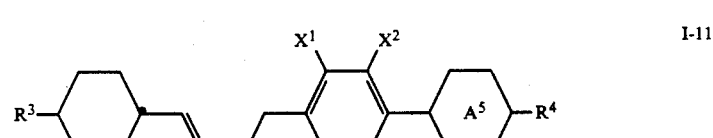

I-11

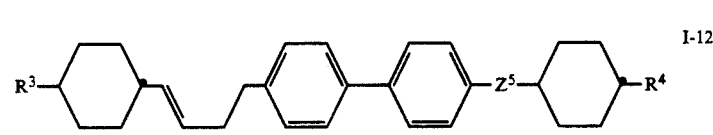

I-12

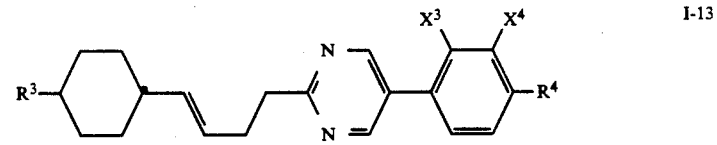

I-13

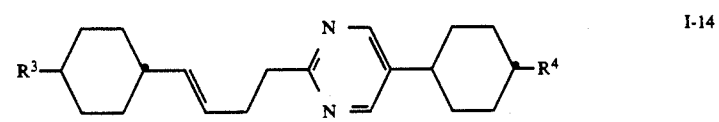

I-14

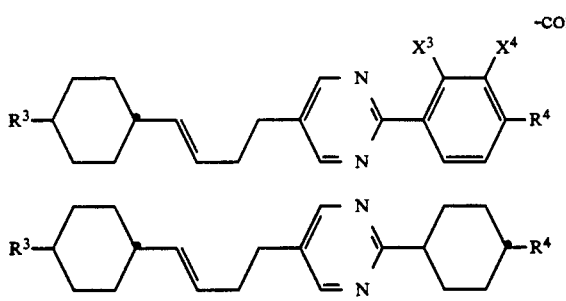

I-15

I-16 wherein $R^3$ and $R^4$ have the above significances, $X^1$, $X^2$, $X^3$ and $X^4$ each independently denote hydrogen, halogen, cyano or methyl, $Z^4$ signifies a single covalent bond, —COO—, —OOC— or —C≡C—; $Z^5$ denotes a single covalent bond, —OOC—, —OCH$_2$—, —CH$_2$—CH$_2$—, —C≡C—, O(CH$_2$)$_3$—, —(CH$_2$)$_4$— or the trans form of —CH$_2$CH$_2$—CH=CH— or —OCH$_2$—CH=CH—; and ring $A^5$ represents pyridine-2,5-diyl, pyrimidine-2,5-diyl, pyrazine-2,5-diyl, trans-1,3-dioxane-2,5-diyl, bicyclo[2.2.2]octane-1,4-diyl, naphthalene-2,6-diyl, tetralin-2,6-diyl or trans-decalin-2,6-diyl.

In general, there are Preferred compounds of formula I without lateral substituents or with lateral fluorine substituents (preferably a maximum of one or two lateral fluorine substituents), i.e. in formulae I-1, I-7 to I-11, I-13 and I-15 above the substituents $X^1$, $X^2$, $X^3$ and $X^4$ preferably stand for hydrogen or fluorine, most preferably, hydrogen, or 1 or 2 of the substituents $X^1$, $X^2$, $X^3$ and $X^4$ also stands for fluorine. It will, however, be evident to a person skilled in the art that in place of fluorine there can also be used other halogen substituents, especially chlorine, and that by lateral methyl substitution the solubility can frequently be improved or by cyano substituents a strong lateral dipole moment can be produced.

In formula I-11 an optionally present pyridine ring, pyrimidine ring, pyrazine ring or 1,3-dioxane ring can be linked in the 2-position or in the 5-position with the benzene ring.

Preferably, a maximum of one of the residues $R^3$ and $R^4$ (preferably $R^4$) stands for halogen, cyano, —NCS, —CF$_3$ or —OCF$_3$, i.e. preferably $R^3$ and $R^4$ each independently denote alkyl in which optionally one >CH—CH< is replaced by >C⊙C< and/or optionally one methylene group or two non-adjacent methylene groups is/are replaced by —O—, —COO— and/or —OOC— and/or optionally one methylene group is replaced by —CHX— or one of the residues $R^3$ and $R^4$ (preferably $R^4$) also denotes halogen, cyano, —NCS, —CF$_3$ or —OCF$_3$ A terminal halogen residue and the —NCS group are preferably present on an aromatic ring, especially a benzene, pyridine, pyrimidine or pyrazine ring.

$R^3$ and $R^4$ in formulae I and I-1 to I-16 above each alkyl group preferably has a maximum of about 18, most preferably, a maximum of about 12 carbon atoms in the chain.

For nematic and cholesteric applications there are generally preferred short residues $R^3$ and $R^4$ (e.g. residues with a maximum of 12, preferably a maximum of 7, carbon atoms) and preferably one of the residues can also signify halogen, cyano, —NCS, —CF$_3$ or —OCF$_3$. For smectic applications (especially tilted smectic phases). Generally preferred are those compounds in which $R^3$ and $R^4$ each independently denote alkyl in which optionally one >CH—CH< is replaced by >C⊙C< and/or optionally one methylene group or two non-adjacent methylene groups is/are replaced by —O—, —COO— and/or —OOC— and/or optionally one methylene group is replaced by —CHX— and the sum of the carbon atoms in $R^3$ and $R^4$ together amounts to at least 10, preferably at least 12.

Preferred residues $R^3$ are alkyl, alkenyl, alkoxy, alkenyloxy, alkoxycarbonyl, alkenyloxycarbonyl, alkanoyloxy and alkenoyloxy, especially alkyl and alkenyl. Residues $R^3$ with up to 12 carbon atoms are generally especially preferred. Especially preferred residues $R^4$ are alkyl, alkenyl, alkoxy, alkenyloxy, alkoxycarbonyl, alkenyloxy- carbonyl, alkanoyloxy and alkenoyloxy (especially alkyl, alkenyl, alkoxy and alkenyloxy) as well as halogen (especially fluorine and chlorine), cyano, —NCS, —CF$_3$ and —OCF$_3$. Residues $R^4$ with up to 12 carbon atoms are generally most preferred.

Straight-chain residues $R^3$ and, respectively, $R^4$ are generally preferred. However, in order to obtain, for example, chiral dopants for cholesteric or for chiral tilted smectic liquid crystals, preferably also one or both residues $R^3$ and $R^4$ can be branched-chain chiral and/or can have a group —CHX— in which X signifies halogen (preferably fluorine or chlorine), cyano or methyl in place of one methylene group. In order to obtain a high spontaneous polarization for chiral tilted smectic applications, the center of chirality (i.e. the chain branching or the halogen or cyano substituent) should preferably be close to the ring system, for example in the 1- or 2-position of the residue $R^3$ or $R^4$. Further, the tendency to form liquid crystalline phases basically remains when 1 methylene group or 2 non-adjacent methylene groups is/are replaced by —O—, —COO- —and/or —OOC—, which can be employed, inter alia, for the preparation of chiral residues from natural, optically active acids, alcohols etc. (e.g. 2-alkoxycarbonylethoxy from lactic acid).

Further, the mesophase range, the threshold potential, the response speed, the steepness of the transmission curve etc. can be varied by the selection of the position of the C=C double bond in unsaturated residues such as alkenyl, alkenyloxy and the like. The effect is fundamentally known e.g. from Mol. Cryst. Liq. Cryst. 122, 241 (1985), 131, 109 (1985) and 148, 123 (1987). There are preferred residues which have the double bond in the 1-position (especially the E-isomer), in the 3-position (especially the E-isomer) or in the 4-position (especially the Z-isomer) of the chain including any hetero atoms, such as 1E-alkenyl, 3E-alkenyl, 4Z-alkenyl, 2E-alkenyloxy, 3Z-alkenyloxy and the like. Further, the double bond can also preferably be in the terminal position, especially in the case of compounds for smectic applications. Examples of preferred residues with the double bond in the terminal position are 6-heptenyl, 7-octenyl, 8-nonenyl, 9-decenyl, 10-undecenyl, 11-dodecenyl, 5-hexenyloxy, 6-heptenyloxy, 7-octenyloxy, 8-nonenyloxy, 9-decenyloxy, 10-undecenyloxy, 11-dodecenyloxy and the like.

The manufacture of the compounds of formula I can be effected in a manner known per se. Preferred methods are illustrated on the basis of the following Schemes 1–4 in which $R^1$, $R^2$, $Z^1$, n and rings $A^1$ and $A^2$ have the above significances, —O—THP denotes tetrahydro-2-pyranyloxy and $R^5$ signifies an alkyl group in which optionally one >CH—CH< is replaced by >C=C< and/or optionally a methylene group which is not present in the 1-position is replaced by —O—, —COO— or —OOC— and/or optionally one methylene group is replaced by —CHX— (wherein X has the above significance).

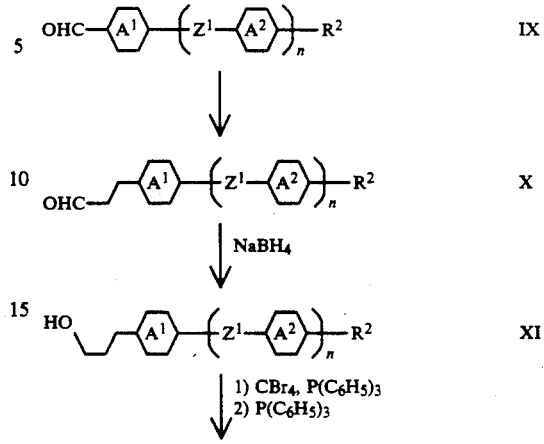

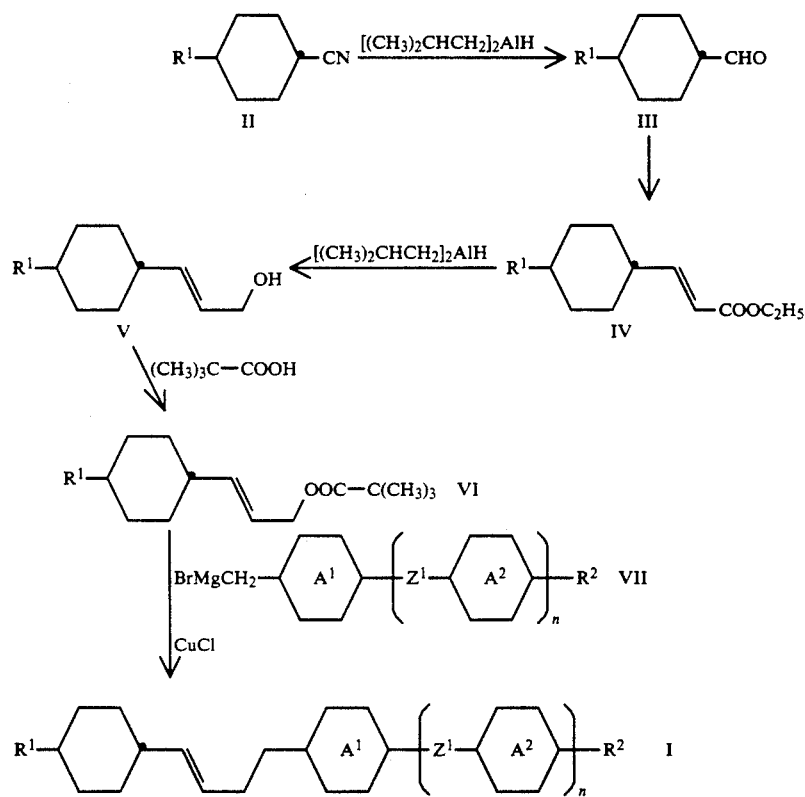

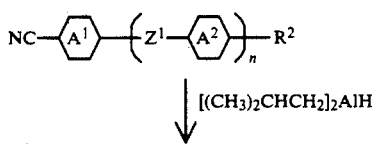

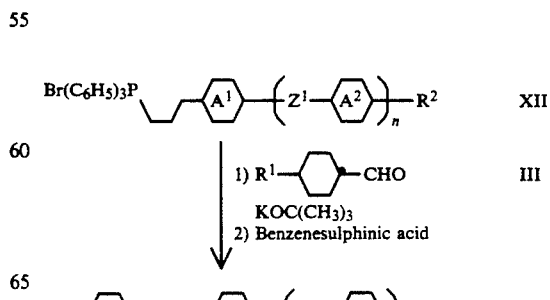

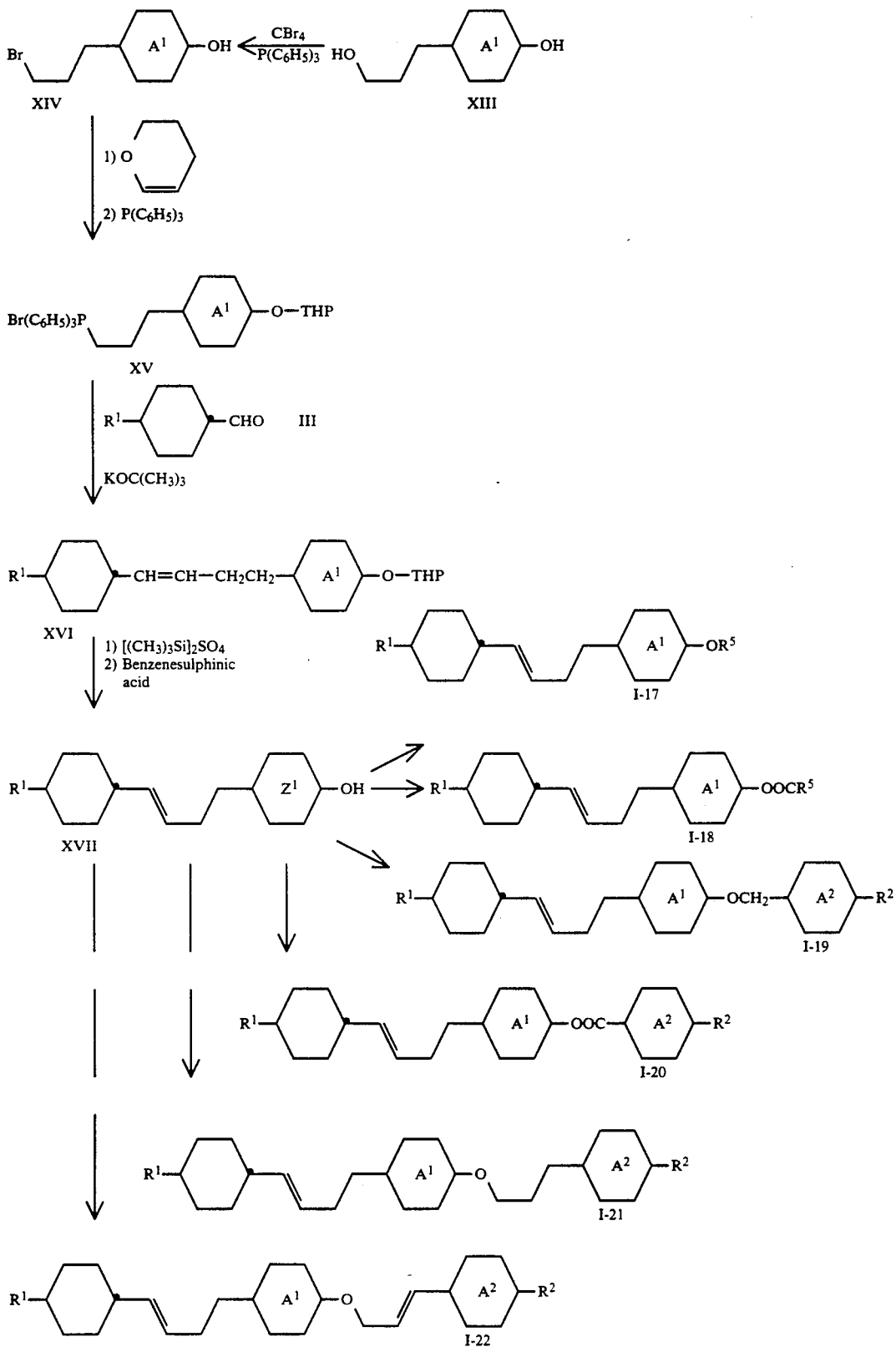

Scheme 4

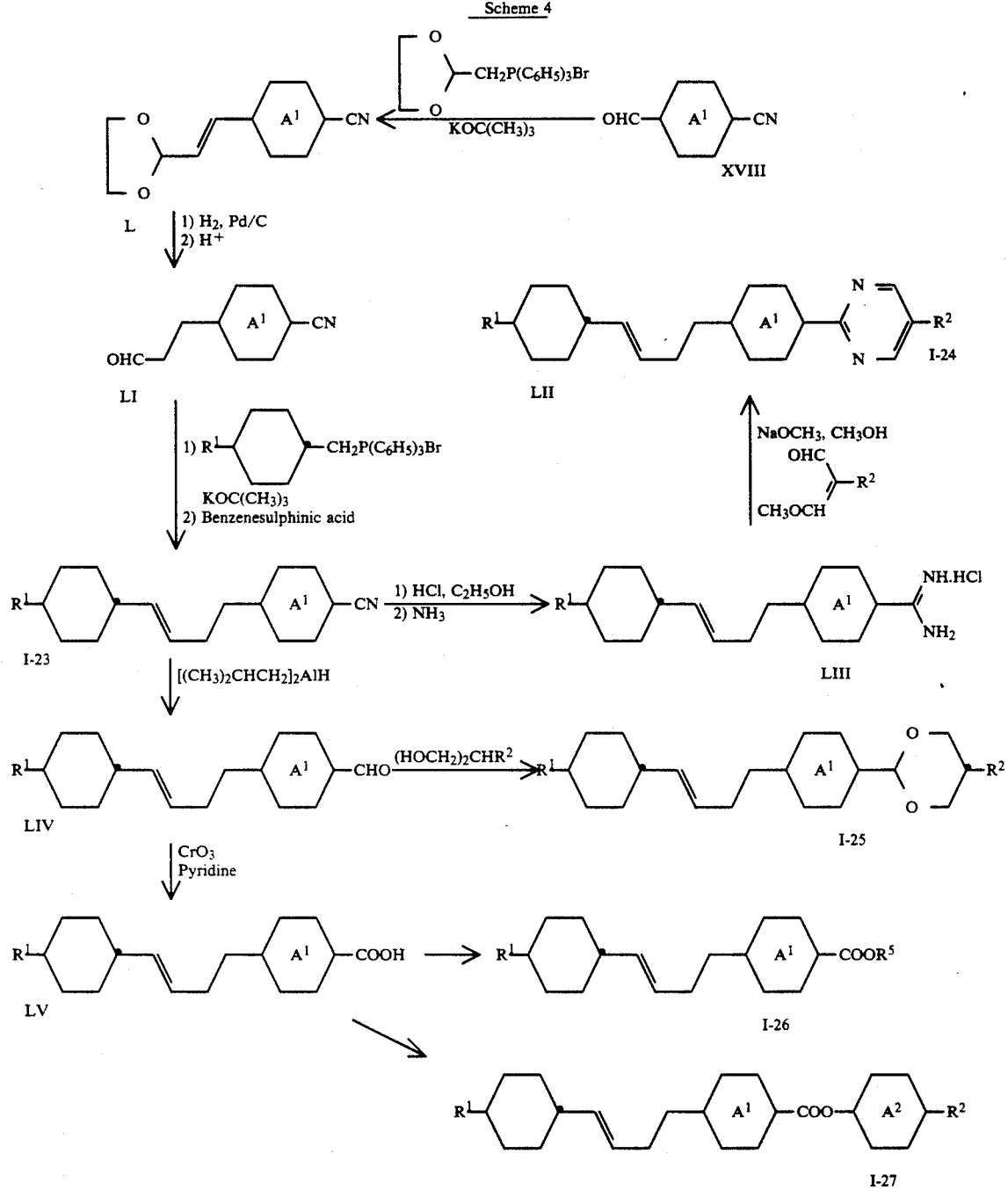

The starting materials of formulae II, III, VIII, IX, X, XIII and XVIII are known compounds or analogues of known compounds and can be prepared according to known methods. Such compounds have already been described as liquid crystals or intermediates for liquid crystals. The preparation of the Grignard reagents of formula VII and of the phosphonium salts of formula LII from the corresponding bromides is readily apparent to a person skilled in the art.

As an alternative to the method given in Scheme 2, the propionaldehyde of formula X can also be reacted—as illustrated in Scheme 4—with the phosphonium salt of formula LII in a Wittig reaction and the resulting cis/trans mixture can be isomerized with benzenesulphinic acid to the compound of formula I.

The methods presented in Schemes 1 and 2 can, of course, also be used for the preparation of intermediates for the compounds of formula I which have a suitable functional group in place of $R^1$, $Z^1$, ring $A^2$ and/or $R^2$. The resulting intermediates having the butene bridging group can subsequently be converted into compounds of formula I in a manner known per se. In particular, the esterification to give compounds of formula I which have one or more ester groups is advantageously effected only after the formation of the butene bridging groups. Of course, other groups such as e.g. alkenyl residues, ether residues, heterocyclic rings can also be formed only subsequently. Examples of such methods are illustrated in Schemes 3 and 4.

The esterification of the compound of formula V can be effected in a manner known per se, e.g. with pivalic acid in the presence of 4-(dimethylamino)pyridine and N,N'-dicyclohexylcarbodiimide or with pivaloyl chloride in the presence of pyridine.

The reaction of the aldehyde of formula IX to give the homologous aldehyde of formula X can be effected according to usual methods. For example, a methylene group can be introduced successively each time by a Wittig reaction of the aldehyde with methoxymethyltriphenylphosphonium chloride and subsequent hydrolysis of the resulting enol ether (e.g. with dilute hydrochloric acid). Direct chain-lengthening by two methylene groups can be achieved according to the method illustrated in Scheme 4 when no readily hydrolyzable groups are present in the molecule.

According to the above method aldehydes can be converted into homologous aldehydes with basically any lengthened chain, which can be used for the manufacture of a wide variety of derivatives. For example, the aldehyde of formula LIV, optionally after conversion into a suitable homologous aldehyde, can be converted by a Wittig reaction into an alkenyl derivative or a compound having a further butene bridging group or can be converted by reaction with 2-$R^2$-1,3-propanediol into dioxane derivatives in which the dioxane ring is linked with ring $A^1$ directly or via —(CH$_2$)$_2$— or —(CH$_2$)$_4$—. By reducing the aldehyde with sodium borohydride or by oxidizing the aldehyde with chromic acid there are also accessible the homologous alcohols or carboxylic acids which can be etherified or esterified in a manner known per se to give compounds of formula I. Examples of suitable etherification and esterification possibilities are illustrated in Schemes 3 and 4 for the compounds of formulae XVII and LV.

Further methods, especially chain-lengthening reactions and methods for the introduction of alkenyl substituents, different bridging groups and heterocyclic rings will be basically known to a person skilled in the art, e.g. from EP-A-0 122 389, EP-A-0 169 327, EP-A-0 172 360, EP-A-0 167 912, EP-A-0 168 683, EP-A-0 242 716 and EP-A-0 344 557.

The compounds of formula I can be used in the form of mixtures with one another and/or with other liquid crystal components. Suitable liquid crystal components are known to a person skilled in the art in large numbers, e.g. from D. Demus et al., Flüssige Kristalle in Tabellen, VEB Deutscher Verlag für Grundstoffindustrie, Leipzig, Volumes I and II, and many of them are, moreover, commercially available.

The invention is accordingly also concerned with a liquid crystalline mixture having at least 2 components, wherein at least one component is a compound of formula I (especially one of the compounds referred to as being preferred).

Having regard to the good solubility and on the other hand to the large breadth of variation of the properties and fields of application, the amount of compounds of formula I in the mixtures in accordance with the invention can vary in a wide range and can amount to about 0.1 to 100 wt.%. For example, the mixture can consist of compounds of formula I. On the other hand, e.g. chiral dopants are frequently used only in relatively small amounts, e.g. about 0.1 to 10 wt.%. In general, however, the amount of compounds of formula I in the mixtures in accordance with the invention amounts to about 1–60 wt.%. A range of about 5–30 wt.% is generally preferred.

The mixtures in accordance with the invention for nematic or cholesteric applications preferably contain, in addition to one or more compounds of the Formula I, one or more compounds from the group of compounds of the general formulae

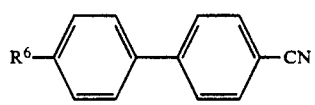

XIX

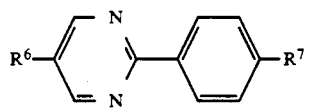

XX

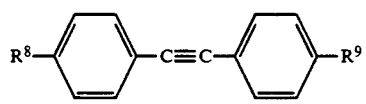

XXI

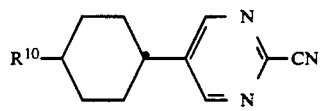

XXII

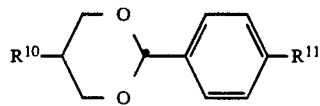

XXIII

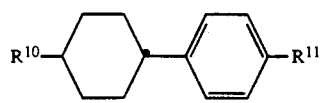

XXIV

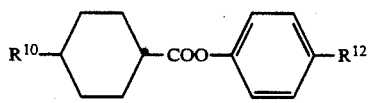

XXV

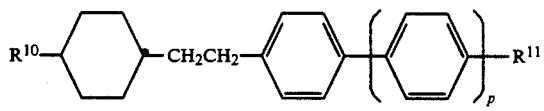

(XXVI)

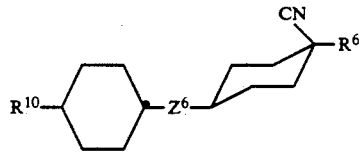

XXVII

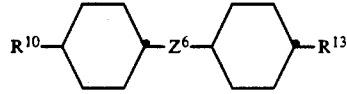

XXVIII

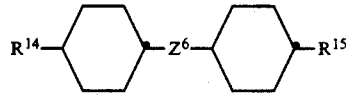

XXIX

XXX

XXXI

XXXII

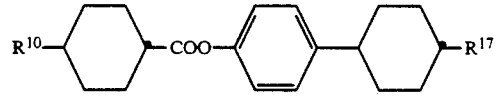

XXXIII

XXXIV

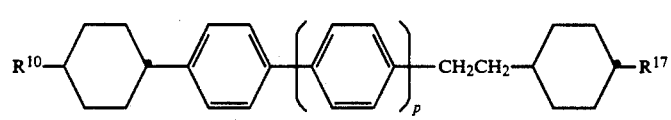

XXXV

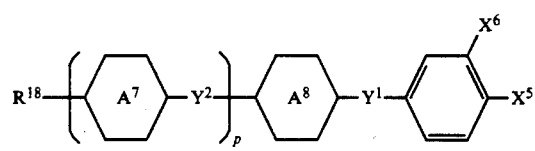

XXXVI wherein $R^6$ signifies alkyl, 3E-alkenyl or 4-alkenyl; $R^7$ represents cyano or fluorine; $R^8$ and $R^9$ denote alkyl or alkoxy; $R^{10}$ and $R^{17}$ each independently signify alkyl, 1E-alkenyl, 3E-alkenyl or 4-alkenyl; denotes cyano, —NCS, alkyl, 3E-alkenyl, 4-alkenyl, alkoxy, 2E-alkenyloxy or 3-alkenyloxy; signifies alkoxy, 2E-alkenyloxy or 3-alkenyloxy; p stands for the number 0 or 1; $Z^6$ represents a single covalent bond or —CH$_2$C-

$H_2$—; $R^{13}$ signifies cyano, alkyl, 1E-alkenyl, 3E-alkenyl or 4-alkenyl; $R^{14}$ denotes alkyl, 1E-alkenyl, 3E-alkenyl or 4-alkenyl; represents alkoxy, 2E-alkenyloxy, 3-alkenyloxy alkoxymethyl or (2-alkenyl)oxymethyl; $R^{16}$ denotes cyano, alkyl, 3E-alkenyl, 4-alkenyl, alkoxy, 2E-alkenyloxy or 3-alkenyloxy; X5 denotes fluorine or chlorine and $X^6$ denotes hydrogen, fluorine or chlorine; $R^{18}$ signifies alkyl, 3E-alkenyl, 4-alkenyl, alkoxy, 2E-alkenyloxy or 3-alkenyloxy; one of the groups $Y^1$ and $Y^2$ signifies a single covalent bond, —COO—, —OOC—, —$CH_2$—$CH_2O$— or —$OCH_2$— and the other of the groups $Y^1$ and $Y^2$ signifies a single covalent bond; and rings $A^7$ and $A^8$ each independently represent trans-1,4-cyclohexylene in which optionally 2 non-adjacent $CH_2$ groups are replaced by oxygen or 1,4-Phenylene in which optionally 1 CH group or 2 CH groups is/are replaced by nitrogen.

Preferably, each of the residues $R^6$ and $R^8$-$R^{18}$ has a maximum of 12 carbon atoms, especially a maximum of 7 carbon atoms. Straight-chain residues are general preferred.

The mixtures in accordance with the invention for smectic applications (especially for tilted smectic or chiral tilted smectic phases) Preferably contain, in addition to one or more compounds of formula I, one or more compounds from the group of compounds of the general formulae

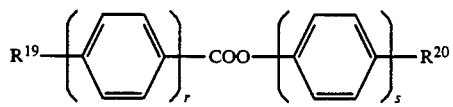

XXXVII

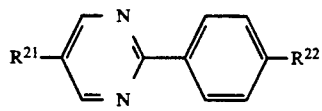

XXXVIII

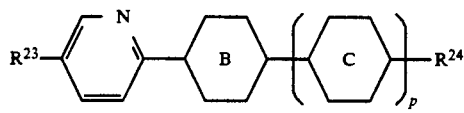

XXXIX

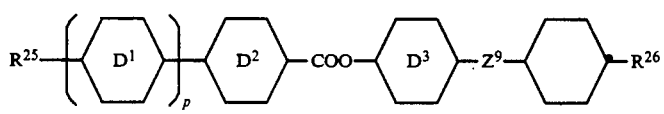

XL

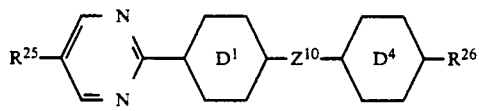

XXXXI

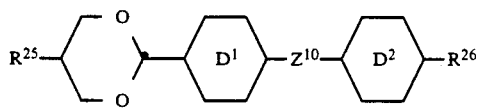

XXXXII

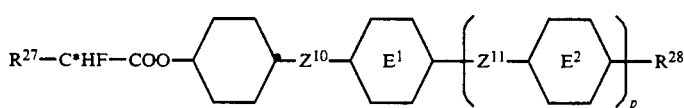

XXXXIII

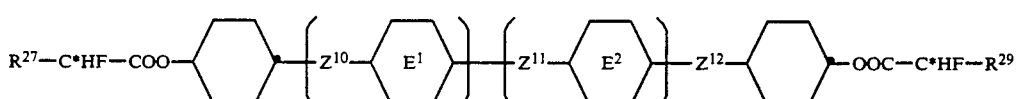

XXXXIV wherein $R^{19}$ and $R^{20}$ denote alkyl, alkoxy, alkenyloxy, alkanoyloxy or alkoxycarbonyl with up to 18 carbon atoms; r and s each independently signify 1 or 2; $R^{21}$ and $R^{22}$ denote alkyl, alkoxy or alkenyloxy with up to 18 carbon atoms; ring B represents unsubstituted or halogen- and/or methyl-substituted 1,4-phenylene; ring C represents trans-1,4-cyclohexylene or unsubstituted or halogen- and/or methyl-substituted 1,4-phenylene; p and q each independently stand for the number 0 or 1; $R^{23}$ and $R^{24}$ each independently denote an unsubstituted or halogen-substituted $C_1$-$C_{18}$-alkyl or $C_2$-$C_{18}$-alkenyl group in which optionally one $CH_2$ group or two non-adjacent $CH_2$ groups is/are replaced by —O—, —COO— and/or —OOC—; rings $D^1$, $D^2$ and $D^3$ each independently represent unsubstituted or cyano-, halogen- or lower alkyl-substituted 1,4-phenylene; $Z^9$ denotes a single covalent bond, —$CH_2CH_2$—, —$OCH_2$, —COO— or —OOC—; $R^{25}$ and $R^{26}$ each independently signify an unsubstituted or halogen-substituted $C_1$-$C_{18}$-alkyl or $C_2$—$C_{18}$-alkenyl group in which optionally one $CH_2$ group or two non-adjacent $CH_2$ groups is/are replaced by oxygen; ring $D^4$ represents trans-1,4-cyclohexylene or unsubstituted or cyano-, halogen- or lower alkyl-substituted 1,4-phenylene; $Z^{10}$, $Z^{11}$ and $Z^{12}$ each independently denote a single covalent bond, —COO—, —OOC—, —CH$_2$CH$_2$—, —OCH$_2$— or —CH$_2$O—; $R^{27}$ and each independently signify a $C_1$-$C_{15}$-alkyl or $C_2$-$C_{15}$-alkenyl group in which optionally one CH$_2$ group is replaced by oxygen; $R^{28}$ denotes an unsubstituted or halogen-substituted $C_1$-$C_{15}$-alkyl or $C_2$-$C_{15}$-alkylene group in which optionally one CH$_2$ group is replaced by oxygen and/or optionally one CH$_2$ group is replaced by an ester group —COO— or —OOC—; rings $E^1$ and $E^2$ each independently represent unsubstituted or halogen-, cyano- and/or methyl-substituted 1,4-phenylene in which optionally 1 CH group or 2 CH groups is/are replaced by nitrogen; and C* denotes a chiral carbon atom.

The manufacture of the liquid crystalline mixtures and of the electro-optical devices can be effected in a manner known per se.

The invention is illustrated in more detail by the following Examples. The optical antipodes of chiral compounds have in each case the same phase transition temperatures and absolutely the same values of the twisting, but with opposite signs. The abbreviations used for the characterization of the phase transitions have the following significances:

C stands for crystalline
S stands for smectic
$S_A$, $S_B$, $S_C$ etc. stand for smectic A, B, C etc.
$S_C^*$, $S_F^*$ etc. stand for chiral smectic C, F etc.
N stands for nematic
N* stands for cholesteric
I stands for isotropic.

EXAMPLE 1

0.12 g of magnesium shavings were covered with 5 ml of absolute diethyl ether while gassing with nitrogen and then, after the addition of a crystal of iodine, covered with a solution of 1.3 g of 4-(trifluoromethoxy)benzyl bromide in 25 ml of diethyl ether. After completion of the addition the mixture was heated to reflux for a further 30 minutes. The reaction mixture was transferred into a dropping funnel and then added dropwise at 0° C. and while gassing with nitrogen to a solution of 0.9 g of 3E-[trans-4-(trans-4-[1E-propenyl]cyclohexyl)-cyclohexyl]-allyl pivalate, 0.03 g of copper-(I) chloride and 25 ml of absolute diethyl ether. After completion of the addition the reaction mixture was stirred at room temperature for a further 30 minutes, then treated with 20 ml of 25% hydrochloric acid and the organic phase was separated. The aqueous phase was extracted three times with 50 ml of diethyl ether each time. The combined organic phases were washed in succession with 500 ml of water, 250 ml of concentrated potassium carbonate solution and again with 500 ml of water, dried over magnesium sulphate, filtered and subsequently concentrated. The residue was purified by chromatography on silica gel with hexane. Recrystallization from acetone gave 0.5 g of pure 1-trifluoromethoxy-4-[4E-(trans-4-(trans-4-[1E-propenyl]cyclohexyl)cyclohexyl)-3-butenyl]benzene with m.p. (C-N) 63° C. and cl.p. (N-1) 149° C.

The 3E-[trans-4-(trans-4-[1E-propenyl]cyclohexyl)-cyclohexyl]-allyl pivalate used as the starting material was prepared as follows:

(a). A solution of 25 g of trans-4-(trans-4-[1E-propenyl]cyclohexyl)cyclohexanecarbonitrile in 50 ml of toluene was treated dropwise at −78° C. while gassing with nitrogen with 150 ml of a 20% solution (wt./vol.) of diisobutylaluminium hydride in toluene. The reaction mixture was stirred at room temperature overnight, then treated with 500 ml of water and subsequently extracted four times with 200 ml of dichloromethane each time. The combined organic phases were washed twice with 500 ml of water, dried over magnesium sulphate, filtered and subsequently concentrated. This gave 20 g of trans-4-(trans-4-[1E-propenyl]cyclohexyl)cyclohexanecarboxaldehyde.

(b). A mixture of 10 g of (trans-4-[1E-propenyl]cyclohexyl)cyclohexanecarboxaldehyde, 12.5 g of ethyl diethylphosphonoacetate $(C_2H_5O)_2PO$-$CH_2COOC_2H_5$, 4.8 g of potassium hydroxide and 100 ml of tetrahydrofuran was stirred for 3 hours and then treated with 500 ml of water and subsequently extracted three times with 100 ml of diethyl ether each time. The combined organic phases were washed twice with 500 ml of water each time, dried over magnesium sulphate, filtered and subsequently concentrated. The residue was purified by chromatography on silica gel with toluene. Recrystallization from hexane gave 12 g of pure ethyl 3E-[trans-4-(trans-4-[1E-propenyl]cyclohexyl)cyclohexyl]acrylate with m.p. (C-N) 40° C. and cl.p. (N-I) 94° C.

(c). A solution of 5 g of 3E-[trans-4-(trans-4-[1E-propenyl]cyclohexyl)cyclohexyl]acrylate in 100 ml of toluene was treated dropwise at 0° C. and while gassing with nitrogen with 50 ml of a 20% solution of diisobutylaluminium hydride in toluene. After completion of the addition the pale yellow solution was stirred for a further 5 hours and then treated cautiously with 50 ml of 25% hydrochloric acid. The reaction mixture was poured into 100 ml of water and the organic phase was separated. The aqueous phase was back-extracted twice with 100 ml of toluene each time. The combined organic phases were washed with 500 ml of water, 500 ml of concentrated potassium hydrogen carbonate solution and again with 500 ml of water and subsequently dried over magnesium sulphate, filtered and concentrated. Recrystallization of the residue from hexane gave 4.2 g of 3E-[trans-4-(trans-4-[1E-propenyl]cyclohexyl)cyclohexyl]allyl alcohol with m.p. (C-$S_B$) 56° C., $S_B$-N 95° C. and cl.p. (N-I) 113° C.

(d). 0.4 g of pivalic acid, 1.0 g of 3E-[trans-4-(trans-4-[1E-propenyl]cyclohexyl)cyclohexyl]allyl alcohol and 0.1 g of 4-(dimethylamino)pyridine were dissolved in 50 ml of dichloromethane and the solution was treated portionwise within 10 minutes while stirring with 0.9 g of N,N'-dicyclohexylcarodiimide. The mixture was stirred at room temperature overnight and then filtered. The filtrate was diluted with dichloromethane, washed twice with 50 ml of saturated sodium carbonate solution each time and then with water, dried over magnesium sulphate, filtered and then concentrated. Chromatography of the residue on silica gel with toluene gave 1.3 g of 3E-[trans-4-(trans-4-[1E-propenyl]cyclohexyl)cyclohexyl]-allyl pivalate.

The following compounds can be manufactured in an analogous manner:

1-Fluoro-4-[4E-(trans-4-pentylcyclohexyl)-3-butenyl]benzene, m.p. (C-I) -6° C., cl.p. (N-I) -13° C.;

1-chloro-4-[4E-(trans-4-pentylcyclohexyl)-3-butenyl]-benzene;

1-bromo-4-[4E-(trans-4-pentylcyclohexyl)-3-butenyl]-benzene;

1-iodo-4-[4E-(trans-4-pentylcyclohexyl)-3-butenyl]-benzene;

1,2-difluoro-4-[4E-(trans-4-pentylcyclohexyl)-3-butenyl]benzene, m.p. (C-I) -11° C., cl.p. (N-I) −33° C.;

1-methyl-4-[4E-(trans-4-pentylcyclohexyl)-3-butenyl]-benzene;

1-(trifluoromethoxy)-4-[4E-(trans-4-pentylcyclohexyl)-3-butenyl]benzene, m.p. (C-I) 5° C., cl.p. (N-I) −17° C.;

1-fluoro-4-[4E-(trans-4-[trans-4-propylcyclohexyl]cyclohexyl)-3-butenyl]benzene, m.p. (C-S$_B$) 33° C., S$_B$-N 74° C., cl.p. (N-I) 135° C.;

1,2-difluoro-4-[4E-(trans-4-[trans-4 -propylcyclohexyl]cyclohexyl)-3-butenyl]benzene, m.p. 27° C., S$_B$-N 50° C., cl.p. (N-I) 119° C.;

1-methyl-4-(4E-(trans-4-[trans-4-propylcyclohexyl]cyclohexyl)-3-butenyl]benzene;

1-(trifluoromethyl)-4-[4E-(trans-4-[trans-4-propylcyclohexyl]cyclohexyl)-3-butenyl]benzene;

1-(trifluoromethoxy)-4-[4E-(trans-4-[trans-4-propylcyclohexyl]cyclohexyl)-3-butenyl]benzene, m.p. (C-S$_B$) 41° C., S 83° C., cl.p. (N-I) 128° C.;

1-fluoro-4-[4E-(trans-4-]trans-4-(1E-propenyl)cyclohexyl]cyclohexyl)-3-butenyl]benzene, m.p. (C-N) 52° C. cl.p. (N-I) 159° C.;

1,2-difluoro-4-[4E-(trans-4-[trans-4-(1E-propenyl)cyclohexyl]cyclohexyl)-3-butenyl]benzene, m.p. (C-N) 60° C., cl.p. (N-I) 140° C.;

1-ethoxy-2,3-difluoro-4-[4E-(trans-4-[trans-4-[propylcyclohexyl]cyclohexyl)-3-butenyl]benzene;

1-fluoro-4-[4E-(trans-4-]trans-4-pentylcyclohexyl]cyclohexyl)-3-butenyl]benzene;

1,2-difluoro-4-[4E-(trans-4-]trans-4-pentylcyclohexyl]-cyclohexyl)-3-butenyl]benzene;

1-methyl-4-[4E-(trans-4-]trans-4-pentylcyclohexyl]cyclohexyl)-3-butenyl]benzene;

1-(trifluoromethyl)-4-[4E-(trans-4-[trans-4-pentylcyclohexyl]cyclohexyl)-3-butenyl]benzene;

1-(trifluoromethoxy)-4-[4E-(trans-4-[trans-4-pentylcyclohexyl]cyclohexyl)-3-butenyl]benzene;

1-ethoxy-2,3-difluoro-4-[4E-(trans-4-[trans-4-pentylcyclohexyl]cyclohexyl)-3-butenyl]benzene;

1-(trans-4-propylcyclohexyl)-4-[4E-(trans-4-propylcyclohexyl)-3-butenyl]benzene;

1-(trans-4-propylcyclohexyl)-4-[4E-(trans-4-pentylcyclohexyl)-3-butenyl]benzene;

1-(trans-4-pentylcyclohexyl)-4-[4E-(trans-4-propylcyclohexyl)-3-butenyl]benzene;

4-(trans-4-propylcyclohexyl)-4'-[4E-(trans-4-propylcyclohexyl)-3-butenyl]biphenyl;

4-(trans-4-propylcyclohexyl)-4'-[4E-(trans-4-pentylcyclohexyl)-3-butenyl]biphenyl;

4-[2(S)-methylbutyloxy]-4'-[4E-(trans-4-pentylcyclohexyl)-3-butenyl]biphenyl;

1-[2-(trans-4-pentylcyclohexyl)-1-ethyl]-4-[4E-(trans-4-pentylcyclohexyl)-3-butenyl]biphenyl;

2-(4-[4E-(trans-4-pentylcyclohexyl)-3-butenyl]-phenyl)-5-propylpyridine;

2-(4-[4E-(trans-4-pentylcyclohexyl)-3-butenyl]-phenyl)-5-butylpyridine;

2-(4-[4E-(trans-4-pentylcyclohexyl)-3-butenyl]-phenyl)-5-pentylpyridine;

2-(4-[4E-(trans-4-pentylcyclohexyl)-3-butenyl]-phenyl)-5-hexylpyridine;

2-(4-[4E-(trans-4-pentylcyclohexyl)-3-butenyl]-phenyl)-5-heptylpyridine;

2-(4-[4E-(trans-4-pentylcyclohexyl)-3-butenyl]-phenyl)-5-octylpyridine;

2-(4-[4E-(trans-4-pentylcyclohexyl)-3-butenyl]-phenyl)-5-nonylpyridine;

2-(4-[4E-(trans-4-pentylcyclohexyl)-3-butenyl]-phenyl)-5-decylpyridine;

5-pentyl-2-[4-(4E-(trans-4-pentylcyclohexyl)-3-butenyl]phenyl]pyrimidine;

5-hexyl-2-[4-[4E-(trans-4-pentylcyclohexyl)-3-butenyl]phenyl]pyrimidine;

5-heptyl-2-[4-[4E-(trans-4-pentylcyclohexyl)-3-butenyl]phenyl]pyrimidine;

5-octyl-2-[4-[4E-(trans-4-pentylcyclohexyl)-3-butenyl]phenyl]pyrimidine;

5-nonyl-2-[4-[4E-(trans-4-pentylcyclohexyl)-3-butenyl]Phenyl]pyrimidine;

5-decyl-2-[4-[4E-(trans-4-pentylcyclohexyl)-3-butenyl]phenyl]pyrimidine;

5-undecyl-2-[4-[4E-(trans-4-pentylcyclohexyl)-3-butenyl]phenyl]pyrimidine;

1-(4-[4E-(trans-4-pentylcyclohexyl)-3-butenyl]-phenyl)-4-pentylbicyclo[2.2.2]octane;

(4aαH,8aβH)-decahydro-2α-(4-[4E-(trans-4-pentylcyclohexyl)-3-butenyl]phenyl)-6β-pentylnaphthalene.

EXAMPLE 2

A mixture of 0.3 g of 4-[4E-(trans-4-pentylhexyl)-3-butenyl]phenol, 0.14 g of methyl iodide, 0.6 g of potassium carbonate and 50 ml of absolute butanone was heated to reflux overnight. Subsequently, the cooled reaction mixture was poured into water and extracted three times with 50 ml of diethyl ether each time. The combined organic phases were washed with 500 ml of water, dried over magnesium sulphate, filtered and concentrated. Chromatography of the residue on silica gel with toluene and recrystallization from ethanol gave pure 1-methoxy-4-[4E-(trans-4-pentylcyclohexyl)-3-butenyl]benzene with m.p. (C-N) 25° C. and cl.p. (N-I) 34° C.

The 4-[4E-(trans-4-pentylhexyl)-3-butenyl]phenol used as the starting material was prepared as follows:

(a). A mixture of 10 g of 3-(4-hydroxyphenyl)-1-propanol, 19 g of triphenylphosphine and 200 ml of dichloromethane was treated dropwise at −18° C. with a solution of 24 g of tetrabromomethane in 100 ml of dichloromethane. The reaction mixture was stirred at room temperature overnight and then concentrated. The residue was purified by chromatography on silica gel with toluene/ethyl acetate (vol. 4:1). This gave 14 g of 3-(4-hydroxyphenyl)-1-propyl bromide.

(b). 5.0 g of 3-(4-hydroxyphenyl)-1-propyl bromide, 2.3 g of 2,3-dihydro-2H-pyran, 0.1 g of bis-(trimethylsilyl) sulphate and 100 ml of absolute dichloromethane were provided and stirred at room temperature for one hour. Subsequently, the reaction mixture was treated with 0.5 ml of absolute pyridine and then concentrated. The liquid residue was purified by chromatography on silica gel with toluene. This gave 4.5 g of 3-(4-[tetrahydro-2-pyranyloxy]phenyl)-1-propyl bromide.

(c). A mixture of 3.0 g of 3-(4-[tetrahydro-2-pyranyloxy]phenyl)-1-propyl bromide, 3.2 g of triphenylphosphine and 5 ml of absolute N,N'-dimethylformamide was heated under slight reflux overnight while gassing with nitrogen. The precipitate formed was filtered off and the cooled filtrate was treated with 10 ml of ethyl acetate, left to stand at 0° C. for 30 minutes and then again filtered. The combined solids were dried under a vacuum. This gave 4.4 g of [3-(4-[tetrahydro-2- pyranyloxy]phenyl)-1-propyl]triphenylphosphonium bromide with m.p. 224°–226° C.

(d) A mixture of 4.0 g of [3-(4-[tetrahydro-2-pyranyloxy]phenyl)-1-propyl]triphenylphosphonium bromide, 1.3 g of trans-4-pentylcyclohexanecarboxaldehyde and 50 ml of absolute tetrahydrofuran was treated portionwise with 0.8 g of solid potassium t-butylate. After completion of the addition the reaction mixture was stirred for a further two hours and then poured into 500 ml of water and extracted three times with 100 ml of diethyl ether each time. The organic phases were washed twice with 500 ml of concentrated sodium chloride solution each time, dried over magnesium sulphate, filtered and subsequently concentrated. Chromatography of the residue on silica gel with toluene gave 1.0 g of 1-[tetrahydro-2-pyranyloxy]-4-[4-(trans-4-pentylcyclohexyl)-3-butenyl]benzene (cis/trans mixture).

(e). A solution of 1.0 g of 1-[tetrahydro-2-pyranyloxy]-4-[4-(trans-4-pentylcyclohexyl)-3-butenyl]benzene, 0.02 g of bis-(trimethylsilyl) sulphate and 25 ml of methanol was stirred for two hours. Subsequently, the reaction mixture was treated with 0.1 ml of pyridine and then concentrated. The liquid residue was purified by chromatography on silica gel with toluene. This gave 0.9 g of 4-[4-(trans-4-pentylcyclohexyl)-3-butenyl]phenol (cis/trans mixture).

(f). A solution of 0.9 g of 4-[4-(trans-4-pentylcyclohexyl)-3-butenyl]phenol in 50 ml of ethanol was treated with a solution of 0.2 g of sodium benzenesulphinate in 1 ml of water and two drops of concentrated hydrochloric acid. The reaction mixture was heated to 65° C. overnight, then treated with 100 ml of water and extracted three times with 50 ml of diethyl ether each time. The combined organic phases were washed twice with 250 ml of concentrated sodium chloride solution each time, dried over magnesium sulphate, filtered and subsequently concentrated. Recrystallization of the residue from hexane gave 0.7 g of 4-[4-(trans-4-pentylcyclohexyl)-3-butenyl]-phenol with m.p. 89°–90° C.

The following compounds can be manufactured in an analogous manner;

1-ethoxy-4-[4E-(trans-4-propylcyclohexyl)-3-butenyl]-benzene;
1-propyloxy-4-[4E-(trans-4-propylcyclohexyl)-3-butenyl]benzene;
1-pentyloxy-4-[4E-(trans-4-propylcyclohexyl)-3-butenyl]benzene;
1-hexyloxy-4-[4E-(trans-4-propylcyclohexyl)-3-butenyl]benzene, m.p. (C-N) 28° C., S -N 36° C., cl.p. (N-I) 40° C.;;
1-heptyloxy-4-[4E-(trans-4-propylcyclohexyl)-3-butenyl]benzene;
1-octyloxy-4-[4E-(trans-4-propylcyclohexyl)-3-butenyl]benzene;
1-ethoxy-4-[4E-(trans-4-pentylcyclohexyl)-3-butenyl]benzene, m.p. (C-N) 34° C., cl.p. (N-I) 51° C.;
1-propyloxy-4-[4E-(trans-4-pentylcyclohexyl)-3-butenyl]benzene, m.p. (C-SB) 32° C., cl.p. (SB-I) 42° C.;
1-butyloxy-4-[4E-(trans-4-pentylcyclohexyl)-3-butenyl]benzene, m.p. (C-SB) 24° C., cl.p. (SB-I) 58° C.;
1-pentyloxy-4-[4E-(trans-4-pentylcyclohexyl)-3-butenyl]benzene, m.p. (C-$S_B$) 28° C., cl.p. ($S_B$-I) 52° C.;
1-hexyloxy-4-[4E-(trans-4-pentylcyclohexyl)-3-butenyl]benzene, m.p. ) 32° C., cl.p. S -I) 56° C.;
1-heptyloxy-4-[4E-(trans-4-pentylcyclohexyl)-3-butenyl]benzene;
1-octyloxy-4-[4E-(trans-4-pentylcyclohexyl)-3-butenyl]benzene;
1-[(trans-4-pentylcyclohexyl)methoxy]-4-[4E-(trans-4-pentylcyclohexyl)-3-butenyl]benzene, m.p. 48° C., cl.p. 125° C.;
1-[3-(trans-4-pentylcyclohexyl)-1-propyloxy]-4-[4E-(trans-4-pentylcyclohexyl)-3-butenyl]benzene, m.p. (C-$S_B$) 110° C., $S_B$-N 114° C., cl.p. (N-I) 122° C.;
1-[3E-(trans-4-pentylcyclohexyl)allyloxy]-4-[4E-(trans-4-pentylcyclohexyl)-3-butenyl]benzene, m.p. (C-$S_Z$) 78° C., $S_Z$-$S_B$ 100° C., $S_B$ 119° C., cl.p. (N-I) 116° C.

EXAMPLE 3

1.7 g of 2,3-difluoro-4-dodecyloxybenzoic acid, 1.5 g of 4-[4E-(trans-4-pentylcyclohexyl)-3-butenyl]phenol and 0.1 g of 4-(dimethylamino)pyridine were dissolved in 250 ml of dichloromethane and the solution was treated portionwise within 10 minutes while stirring with ½ g of N,N'-dicyclohexylcarbodiimide. The mixture was stirred at room temperature overnight and then filtered. The filtrate was diluted with dichloromethane, washed twice with 50 ml of saturated sodium carbonate solution each time and then with 100 ml of water, dried over magnesium sulphate, filtered and then concentrated. Chromatography of the residue on silica gel with toluene and recrystallization from ethanol gave 2 g of 2,3-difluoro-4-dodecyloxybenzoic acid 4-[4E-(trans-4-pentylcyclohexyl)-3-butenyl]phenyl ester with m.p. (C-$S_C$) 51° C., $S_C$-N 115° C. and cl.p. (N-I) 133° C.

The following compounds can be manufactured in an analogous manner:

2,3-Difluoro-4-heptyloxybenzoic acid 4-[4E-(trans-4-pentylcyclohexyl)-3-butenyl]phenyl ester, m.p. (C-$S_C$) 55° C., $S_C$-N 77° C., cl.p. (N-I) 140° C.;
2,3-difluoro-4-octyloxybenzoic acid 4-[4E-(trans-4-pentylcyclohexyl)-3-butenyl]phenyl ester, m.p. (C-$S_C$) 75° C., $S_C$-N 88° C., cl.p. (N-I) 140° C.;
2,3-difluoro-4-nonyloxybenzoic acid 4-[4E-(trans-4-pentylcyclohexyl)-3-butenyl]phenyl ester, m.p. (C-$S_C$) 77° C., $S_C$-N 99° C., cl.p. (N-I) 137° C.;
2,3-difluoro-4-decyloxybenzoic acid 4-[4E-(trans-4-pentylcyclohexyl)-3-butenyl]phenyl ester, m.p. (C-$S_C$) 72° C., $S_C$-N 106° C., cl.p. (N-I) 136° C.;
2,3-difluoro-4-undecyloxybenzoic acid 4-[4E-(trans-4-pentylcyclohexyl)-3-butenyl]phenyl ester, m.p. (C-$S_C$) 60° C., $S_C$-N 111° C., cl.p. (N-I) 134° C.; trans-4-propylcyclohexanecarboxylic acid 4-[4E-(trans-4-pentylcyclohexyl)-3-butenyl]phenyl ester;
trans-4-pentylcyclohexanecarboxylic acid 4-[4E-(trans-4-pentylcyclohexyl)-3-butenyl]phenyl ester;
trans-4-heptylcyclohexanecarboxylic acid 4-[4E-(trans-4-pentylcyclohexyl)-3-butenyl]phenyl ester.

EXAMPLE 4

A mixture of 14 g of 3-(4-cyanophenyl)propionaldehyde, 54 g of (trans-4-pentylcyclohexyl)methyl-triphenylphosphonium bromide, 11 g potassium t-butylate and 500 ml of absolute tetrahydrofuran was reacted in an analogous manner to Example 2 (d). There were thus obtained 16 g of 4-[4-(trans-4-pentylcyclohexyl)-3-butenyl]benzonitrile as a cis/trans mixture.

A mixture of 16 g of 4-[4-(trans-4-pentylcyclohexyl)-3-butenyl]benzonitrile (cis/trans mixture), 50 ml of ethanol and 1.9 g of benzenesulphinic acid (freshly prepared from 13 ml of water, 2.0 g of sodium benzene-sulphinate and 5 drops of concentrated hydrochloric acid) was reacted in an analogous manner to Example 2 (f). There were thus obtained 11 g of 4-[4E-(trans-4-pentylcyclohexyl)-3-butenyl]benzonitrile; m.p. (C-N) 40° C., cl.p. (N-I) 45° C.

The 3-(4-cyanophenyl)propionaldehyde used as the starting material was prepared as follows:

(a). A mixture of 20 g of 4-cyanobenzaldehyde, 79 g of 1,3-dioxolan-2-yl)methyl-triphenylphosphinium bromide, 19 g of potassium t-butylate and 500 ml of absolute tetrahydrofuran was reacted in an analogous manner to Example 2 (d). There were thus obtained 20 g of 4-[2-(1,3-dioxolan-2-yl)vinyl]benzonitrile as a cis/trans mixture.

(b). A mixture of 20 g of 4-[2-(1,3-dioxolan-2-yl)vinyl]benzonitrile (cis/trans mixture), 200 ml of absolute toluene and 100 ml of absolute ethyl acetate was treated with 2 g of palladium/carbon (10%) and hydrogenated at normal pressure and room temperature until finished. The inorganic material was filtered off and the filtrate was concentrated. The residue was purified by chromatography on silica gel with toluene/ethyl acetate (vol. 4:1). This gave 19 g of 4-[3-(1,3-dioxolan-2-yl)ethyl]benzonitrile.

(c). A mixture of 19 g of 4-[3-(1,3-dioxolan-2-yl)ethyl]benzonitrile, 10 ml of formic acid and 100 ml of absolute toluene was stirred at room temperature overnight. The reaction mixture was washed with 200 ml of water and then with 75 ml of saturated sodium carbonate solution, dried over magnesium sulphate, filtered and subsequently concentrated. This gave 14 g of 3-(4-cyanophenyl)propionaldehyde.

The following compounds can be manufactured in an analogous manner:

4-[4E-(trans-4-Methylcyclohexyl)-3-butenyl]benzonitrile;

4-[4E-(trans-4-ethylcyclohexyl)-3-butenyl]benzonitrile;

4-[4E-(trans-4-propylcyclohexyl)-3-butenyl]benzonitrile;

4-[4E-(trans-4-butylcyclohexyl)-3-butenyl]benzonitrile;

4-[4E-(trans-4-hexylcyclohexyl)-3-butenyl]benzonitrile;

4-[4E-(trans-4-heptylcyclohexyl)-3-butenyl]benzonitrile;

4-[4E-(trans-4-octylcyclohexyl)-3-butenyl]benzonitrile;

4-[4E-(trans-4-propylcyclohexyl)-3-butenyl]04'-cyanobiphenyl;

4-[4E-(trans-4-pentylcyclohexyl)-3-butenyl]-4'-cyanobiphenyl;

4-[4E-(trans-4-heptylcyclohexyl)-3-butenyl]-4'-cyanobiphenyl;

EXAMPLE 5 a solution of 3 g of 4-[4E-(trans-4-pentylcyclohexyl)-3-butenyl]benzaldehyde and 1.7 g of 2-pentyl-1,3-propanediol in 50 ml of toluene was treated with 2 drops of 10% (vol.) sulphuric acid. The mixture was heated to boiling for 2 hours, whereby the resulting water was simultaneously distilled off. Then, 4 drops of triethylamine were added to the reaction mixture. After cooling the mixture was washed with 50 ml of 1N sodium hydrogen carbonate solution and twice with 50 ml of water each time, dried over magnesium sulphate, filtered and subsequently concentrated. Chromatography of the residue on silica gel with toluene and recrystallization from acetone gave 1.2 g of trans-5-pentyl-2-(4-[4E-(trans-4-pentylcyclohexyl)-3-butenyl]phenyl-1,3-dioxane.

The 4-[4E-(trans-4-pentylcyclohexyl)-3-butenyl]benzaldehyde used as the starting material was prepared as follows:

A solution of 10 g of 4-[4E-(trans-4-pentylcyclohexyl)-3-butenyl]benzonitrile in 200 ml of absolute dichloromethane was treated at −78° C. and while gassing with nitrogen with 50 ml of a solution of diisobutylaluminium hydride in hexane (vol. 20%). After completion of the addition the reaction mixture was stirred at room temperature for a further 8 hours and then treated with 200 ml of water and extracted three times with 100 ml of dichloromethane each time. The combined organic phases were washed twice with 500 ml of water each time, dried over magnesium sulphate, filtered and concentrated. This gave 7.5 g of 4-[4E-(trans-4-pentylcyclohexyl)-3-butenyl]benzaldehyde.

The following compounds can be manufactured in an analogous manner:

trans-5-Propyl-2-(4-[4E-(trans-4-propylcyclohexyl)-3-butenyl]phenyl)-1,3-dioxane;

trans-5-propyl-2-(4-[4E-(trans-4-pentylcyclohexyl)-3-butenyl]phenyl)-1,3-dioxane;

trans-5-pentyl-2-(4-[4E-(trans-4-propylcyclohexyl)-3-butenyl]phenyl)-1,3-dioxane.

EXAMPLE 6

2 g of 4-[4E-(trans-4-pentylcyclohexyl)-3-butenyl]benzoic acid, 0.7 g of 4-fluorophenol, 1.5 g of N,N'-dicyclohexylcarbodiimide, 0.1 g of 4-(dimethylamino)-pyridine and 100 ml of dichloromethane were reacted in an analogous manner to Example 3. This gave 1.8 g of 4-[4E-(trans-4-pentylcyclohexyl)-3-butenyl]-benzoic acid 4-fluorophenyl ester.

The 4-[4E-(trans-4-pentylcyclohexyl)-3-butenyl]benzoic acid used as the starting material was prepared as follows:

A solution of 4 g of 4-[4E-(trans-4-pentylcyclohexyl)-3-butenyl]benzaldehyde (prepared according to Example 5) in 100 ml of acetone was treated dropwise with 10 ml of Jones' reagent. The mixture was stirred at room temperature for 1 hour and then poured into 100 ml of water. The precipitate which thereby resulted was filtered off, washed portionwise with water and dried in a vacuum. The crude product was recrystallized from ethanol and gave 2.5 g of pure 4-[4E-(trans-4-pentylcyclohexyl)-3-butenyl]benzoic acid.

The following compounds can be manufactured in an analogous manner:

4-[4E-(trans-4-Pentylcyclohexyl)-3-butenyl]benzoic acid 4-chlorophenyl ester;

4-[4E-(trans-4-pentylcyclohexyl)-3-butenyl]benzoic acid 4-bromophenyl ester;

4-[4E-(trans-4-pentylcyclohexyl)-3-butenyl]benzoic acid 4-iodophenyl ester;

4-[4E-(trans-4-pentylcyclohexyl)-3-butenyl]benzoic acid 4-cyanophenyl ester, m.p. (C-N) 76° C., cl.p. (N-I) 171° C.;

4-[4E-(trans-4-pentylcyclohexyl)-3-butenyl]benzoic acid 2-fluoro-4-cyanophenyl ester;

4-[4E-(trans-4-pentylcyclohexyl)-3-butenyl]benzoic acid 3-fluoro-4-cyanophenyl ester, m.p. (C-N) 63° C., cl.p. (N-I) 149° C.;

4-[4E-(trans-4-pentylcyclohexyl)-3-butenyl]benzoic acid 3,4-difluorophenyl ester, m.p. (C-N) 40° C., cl.p. (N-I) 104° C.;

4-[4E-(trans-4-pentylcyclohexyl)-3-butenyl]benzoic acid 4-trifluoromethoxyphenyl ester, m.p. (C-N) 70° C., cl.p. (N-I) 128° C.

4-[4E-(trans-4-pentylcyclohexyl)-3-butenyl]benzoic acid 2,3-difluoro-4-ethoxyphenyl ester;

4-[4E-(trans-4-pentylcyclohexyl)-3-butenyl]benzoic acid 2,3-dicyano-4-pentylphenyl ester;

4-[4E-(trans-4-pentylcyclohexyl)-3-butenyl]benzoic acid 4-methylphenyl phenyl ester:

4-[4E-(trans-4-pentylcyclohexyl)-3-butenyl]benzoic acid 4-propylphenyl ester;

4-[4E-(trans-4-pentylcyclohexyl)-3-butenyl]benzoic acid 4-pentylphenyl ester;

4-[4E-(trans-4-pentylcyclohexyl)-3-butenyl]benzoic acid trans-4-propylcyclohexyl ester.

I claim:

1. Compounds of the formula

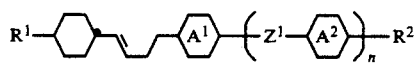

I wherein n stands for the number 0 or 1; ring $A^1$ is 1,4-phenylene which may be unsubstituted or substituted with one or more of halogen, cyano or methyl, or ring $A^1$ is pyridin-2,5-diyl, pyrimidin-2,5-diyl, pyrazin-2,5-diyl, or pyridazin-3,6-diyl, ring $A^2$ represents 1,4-phenylene which may be unsubstituted or substituted with one or more of halogen, cyano and methyl, or ring $A^2$ is pyridin-2,5-diyl, pyrimidin-2,5-diyl, pyrazin-2,5-diyl, pyradizin-3,6-diyl, or ring $A^2$ is trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,5-diyl or trans-decalin-2,6-diyl; $Z^1$ signifies a single covalent bond, —COO—, —OOC—,—CH$_2$O—, —OCH$_2$—, —CH$_2$CH$_2$—, —C≡C—, —(CH$_2$)$_3$O—, —O(CH$_2$)$_3$—, —(CH$_2$)$_4$— or the trans form of —CH=CH—CH$_2$CH$_2$—, —CH$_2$CH$_2$—CH=CH—, —CH=CH—CH$_2$O— or —OCH$_2$—CH=CH—; $R^1$ and $R^2$ each independently denote halogen, cyano, —CF$_3$, —OCF$_3$ or an alkyl or alkenyl of up to 18 carbon atoms in which optionally one methylene group or two non-adjacent methylene groups may be replaced by —O—, —COO— and/or —OOC— and/or optionally one methylene group is replaced by —CHX—; and X signifies halogen, or methyl.

2. Compounds according to claim 1, having the formula

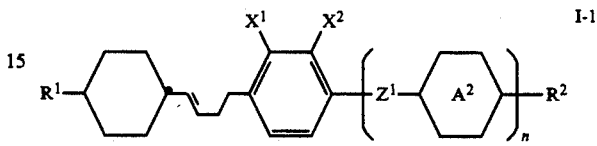

I-1 wherein n, $R^1$, $R^2$, $z^1$ and ring $A^2$ have the significances given in claim 1 and $X^1$ and $X^2$ each independently denote hydrogen, halogen, cyano or methyl.

3. Compounds according to claim 1, wherein ring $A^2$ stands for unsubstituted 1,4-phenylene or 1,4-phenylene monosubstituted or 2,3-disubstituted with halogen, cyano and/or methyl, or trans-1,4-cyclohexylene, trans-1,3-dioxane-2,5-diyl, 1-cyano-trans-1,4-cyclohexylene, bicyclo[2.2.2]octane-1,4-diyl, naphthalene-2,6-diyl, tetralin-2,6-diyl, trans-decalin-2,6-diyl, pyridine-2,5-diyl, pyrimidine-2,5-diyl or pyrazine-2,5-diyl.

4. Compounds according to claim 1, wherein $Z^1$ signifies a single covalent bond, —COO—, —OOC—, —CH$_2$O—, —OCH$_2$—, —CH$_2$CH$_2$—, —C≡C—, —(CH$_2$)$_3$O—, —O(CH$_2$)$_3$—, —(CH$_2$)$_4$— or the trans form of —CH=CH—CH$_2$CH$_2$—, —CH$_2$CH$_2$—CH=CH—, —CH=CH—CH$_2$O— or —OCH$_2$—CH=CH—.

5. Compounds according to claim 1, having the formulae

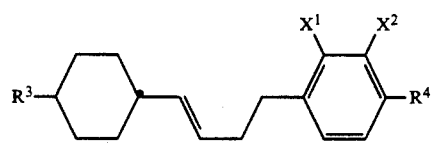

I-7

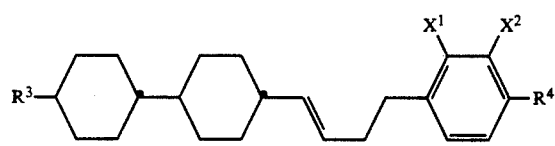

I-8

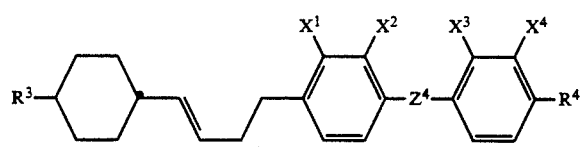

I-9

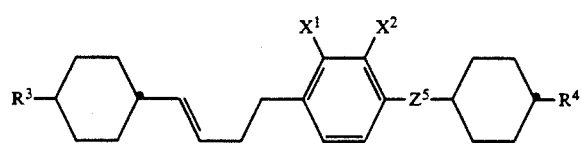

I-10

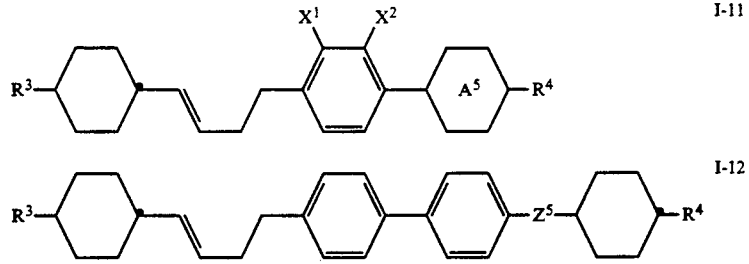

wherein R³ and R⁴ have the significances of R¹ and R² respectively given in claim 1; X¹, X², X³ and X⁴ each independently denote hydrogen, halogen, cyano or methyl, Z⁴ signifies a single covalent bond, —COO—, —OOC— or —C≡C—; Z⁵ denotes a single covalent bond, —OOC—, —OCH₂—, —CH₂CH₂—, —C≡C—, —O(CH₂)₃—, —(CH₂)₄— or the trans form of —CH₂CH₂—CH=CH— or OCH₂—CH=CH—; and ring A⁵ represents pyridine-2,5-diyl, pyrimidine-2,5-diyl, pyrazine-2,5-diyl, trans-1,3-dioxane-2,5-diyl, bicyclo[2.2.2]octane-1,4-diyl, naphthalene-2,6-diyl, tetralin-2,6-diyl or trans-decalin-2,6-diyl.

6. Compounds according to claim 5, wherein X¹, X², X³ and X⁴ each independently signify hydrogen or fluorine.

7. Compounds according to claim 1, wherein R¹ and R² each independently denote an alkyl or alkenyl of up to 18 carbon atoms in which optionally one methylene group or two non-adjacent methylene groups may be replaced by —O—, —COO—an/or —OOC— and/or optionally one methylene group is replaced by —CHX— where X signifies halogen or methyl or R⁴ denotes halogen, cyano, —CF₃ or —OCF₃.

8. Compounds according to claim 1, wherein R¹ signifies alkyl, alkenyl, alkoxy, alkenyloxy, alkoxycarbonyl, alkenyloxycarbonyl, alkanoyloxy or alkenoyloxy.

9. Compounds according to claim 1, wherein R² signifies alkyl, alkenyl, alkoxy, alkenyloxy, alkoxycarbonyl, alkenyloxycarbonyl, alkanoyloxy, alkenoyloxy, halogen, cyano, —CF₃ or —OCF₃.

10. A liquid crystalline mixture with at least 2 components, wherein at least one component is a compound of formula I defined in claim 1.

* * * * *